United States Patent
Galbraith

(10) Patent No.: US 7,790,475 B2
(45) Date of Patent: Sep. 7, 2010

(54) APPARATUSES AND METHODS FOR REDUCING ALBUMIN IN SAMPLES

(75) Inventor: William Galbraith, Paxton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 528 days.

(21) Appl. No.: 10/922,560

(22) Filed: Aug. 19, 2004

(65) Prior Publication Data
US 2005/0074870 A1 Apr. 7, 2005

Related U.S. Application Data

(60) Provisional application No. 60/506,634, filed on Sep. 25, 2003, provisional application No. 60/506,579, filed on Sep. 26, 2003, provisional application No. 60/531,377, filed on Dec. 19, 2003.

(51) Int. Cl.
*G01N 33/538* (2006.01)

(52) U.S. Cl. .................. 436/541; 436/518; 436/528; 436/529; 436/536; 436/538; 435/7.1; 435/174; 435/283.1; 435/287.2; 435/288.6

(58) Field of Classification Search .............. 436/518, 436/528, 529, 536, 538, 174, 177, 541; 422/50, 422/61, 99, 101, 102, 104, 311, 178; 435/4, 435/7.1, 174, 283.1, 287.2, 288.6, 288.7
See application file for complete search history.

(56) References Cited

U.S. PATENT DOCUMENTS

| | | | | |
|---|---|---|---|---|
| 4,061,466 A | * | 12/1977 | Sjoholm et al. | 436/535 |
| 4,093,612 A | | 6/1978 | Travis et al. | |
| 5,506,144 A | * | 4/1996 | Sundrehagen | 436/66 |
| 5,567,615 A | * | 10/1996 | Degen et al. | 435/280 |
| 5,643,721 A | * | 7/1997 | Spring et al. | 435/6 |
| 6,613,884 B1 | * | 9/2003 | Johansson | 530/364 |
| 2002/0127739 A1 | * | 9/2002 | Pieper et al. | 436/515 |
| 2003/0032000 A1 | * | 2/2003 | Liu et al. | 435/4 |
| 2005/0042772 A1 | * | 2/2005 | Naylor et al. | 436/518 |

FOREIGN PATENT DOCUMENTS

EP 0 469 519 A2 2/1992

OTHER PUBLICATIONS

Grahnen et al., The preparation of Ligandin with Glutathione-S-Transferase Activity from Porcine Liver Cytosol by Affinity Chromatography on Bromosulphophthalein-Sepharose, Eur. J. Biochem, 1977, vol. 80, pp. 573-580.*

Wolkoff, A. W. et al.: "Purification of Ligandin by Affinity Chromatography on Sulfobromophthalein-Agarose Gel." Proceedings of the Society for Experimental Biology and Medicine, Society for Experimental Biology and Medicine (New York, N.Y.) Feb. 1979, vol. 160, No. 2, pp. 150-153 XP008040124, ISSN: 0037-9727.

(Continued)

*Primary Examiner*—Melanie Yu
(74) *Attorney, Agent, or Firm*—Hoffmann & Baron, LLP

(57) ABSTRACT

The present invention is directed to apparatuses and methods for reducing the content of albumin in serum, plasma and/or blood samples. The apparatuses comprise an insoluble support with a ligand attached thereto. According to certain embodiments of the invention, the ligand is a bromosulfophthalein, Cibacron Blue or Warfarin ligand or salts or esters thereof. Also provided are methods of making the apparatus, as well as kits and albumin-depleted samples produced by the methods of the present invention.

14 Claims, 10 Drawing Sheets

OTHER PUBLICATIONS

Travis, J. et al.: "Isolation of Albumin From Whole Human Plasma and Fractionation of Albumin-Depleted Plasma." The Biochemical Journal, Aug. 1, 1976, vol. 157, No. 2, pp. 301-306, XP008040119, ISSN: 0264-6021.

Steel, Laura F et al.: "Efficient and Specific Removal of Albumin from Human Serum Samples." Molecular & Cellular Proteomics: MCP. Apr. 2003, vol. 2, No. 4, pp. 262-270, XP002309638, ISSN: 1535-9476.

Stremmel et al., "Physiochemical and Immunohistologcal studies of sulfobromopthalein and bilirubin-binding protein from rat liver plasma membranes," J. Clin. Invest, vol. 71, pp. 1796-1805 (1983).

Reichen et al., "Isolation of an Organic Anion-binding protein from rat liver plasma membrane fractions by affinity chromatography," Biochem. Biophys. Res. Commun., vol. 91, pp. 484-489 (1979).

Clark et al., "Affinity Chromatography of Rat Plasma Albumin on Bromosulfophthalein-Glutathione Conjugate Covalently Linked to Sepharose 4-B," Analytical Biochemistry, vol. 92, pp. 290-293 (1979).

Zamora et al., "Preparation of new gels derived from poly(sucrose acrylate) with immobilized Cibacron Blue and their application in affinity chromatography," Polymer Bulletin, vol. 37, pp. 483-488 (1996).

* cited by examiner

SET 1: BST MATRIX, MONTAGE COLUMN, PBS BUFFER W/0.05% TWEEN 20
SET 2: "MONTAGE MATRIX", MATRIX COLUMN
SET 3: "MONTAGE MATRIX" BioRad COLUMN
SET 4: BST MATRIX, MONTAGE COLUMN, PBS BUFFER

APPARATUSES AND METHODS FOR REDUCING ALBUMIN IN SAMPLES

RELATED APPLICATIONS

This application claims the benefit of U.S. Provisional Application No. 60/506,634 filed on Sep. 25, 2003, U.S. Provisional Application No. 60/506,579 filed on Sep. 26, 2003, and U.S. Provisional Application No. 60/531,377 filed on Dec. 19, 2003, all of which are hereby incorporated by reference in their entirety.

FIELD OF THE INVENTION

The present invention is directed to albumin-depleted samples. More particularly, the present invention relates to an apparatus for reducing the content of albumin in serum, plasma, and/or blood samples. The apparatus comprises an insoluble support with a ligand attached thereto. The present invention also relates to methods for producing albumin-depleted samples. The methods of the present invention include methods for handling a serum, plasma, and/or blood sample containing albumin and for reducing the content of the albumin in a sample so as to provide an albumin-depleted sample. Further included are methods of providing samples depleted of albumin and/or one or more additional proteins, as well as protein-depleted samples produced by such methods.

BACKGROUND OF THE INVENTION

Human Serum Albumin (HSA) constitutes 57-71% of total serum protein. Depletion or removal of HSA provides several advantages including allowing for the enhanced detection of the remaining proteins that are present in lower concentration.

Typically, albumin has been removed from serum or plasma by one of two methods. First, albumin may be removed by antibodies using standard affinity chromatography. An advantage of standard affinity chromatography may be theoretical specificity and tight ligand association and binding. Disadvantages include the high cost and the possibility of immobilization and, hence, depletion of additional proteins through secondary interactions. A second method involves the use of Cibacron Blue attached to typical column matrices such as Sephadex. For example, so-called "swell-gel" columns are currently sold for albumin depletion based on the Cibacron Blue bonding. This method has disadvantages in that it achieves weaker binding of the albumin, and many other proteins also bind to the dye, i.e., lack of specificity. Cibacron Blue bonding is described in further detail by S. T. Thompson, et al., "Blue Dextran-Sepharose: An Affinity Column for the Dinucleotide Fold in Proteins," *Proc. Natl. Acad. Sci.* 72: 669-672 (1975) and J. Travis, et al., "Isolation of Albumin from Whole Human Plasma and Fractionation of Albumin-Depleted Plasma," *Biochem. J* 157: 301-306 (1976).

Attempts have been made to more specifically bind HSA to a support and thereby reduce the albumin content in serum. For example, a method has been described using an antibody ligand to bind human serum albumin. This ligand is disadvantageous in that the capacity of the device is quite low.

Thus, there exists in the art a need for an effective method of depleting albumin from blood, serum and/or plasma samples.

SUMMARY OF THE INVENTION

It has now been found that albumin, such as HSA, may be separated out of blood, serum and/or plasma samples with higher specificity and less non-specific binding of non-albumin proteins than by other known methods by attaching a ligand capable of preferentially binding albumin, such as bromosulfophthalein (BSP) or another suitable ligand, to an insoluble support and running a sample containing albumin over the support.

The present invention is directed to an apparatus and method for reducing the content of albumin in serum, plasma and/or blood samples. An apparatus in accordance with the present invention includes an insoluble support having a suitable ligand, such as a ligand capable of preferentially binding albumin, e.g., a BSP ligand, attached thereto. Methods of producing an albumin-depleted sample in accordance with the present invention include providing a sample; running the sample over an insoluble support having a ligand capable of preferentially binding albumin attached thereto; and allowing albumin to bind to the ligand to provide an albumin-depleted sample. The methods of the present invention may further include methods of providing a protein-depleted sample, which is depleted of albumin and/or one or more additional proteins, as well as protein-depleted samples produced by such methods.

The present inventor has also discovered advantageous methods of binding such ligands to the insoluble support. These methods include, for example, bringing a ligand capable of preferentially binding albumin into contact with epoxy-activated sepharose beads under alkaline conditions, in which the hydrogen is removed from the ligand and the anion is able to react with the epoxy. Accordingly, another aspect of the present invention is a method for making an apparatus for reducing the content of albumin in a serum, plasma and/or blood sample, which method includes attaching a ligand capable of preferentially binding albumin to an insoluble support, such as sepharose beads. Further provided are kits including various components of the apparatus of the present invention, such kits comprise an insoluble support having attached thereto a ligand capable of preferentially binding albumin.

Also provided are spin columns, kits including spin columns, and methods for producing an albumin-depleted sample using a spin column in accordance with the present invention.

DETAILED DESCRIPTION OF THE INVENTION

Figure 1:
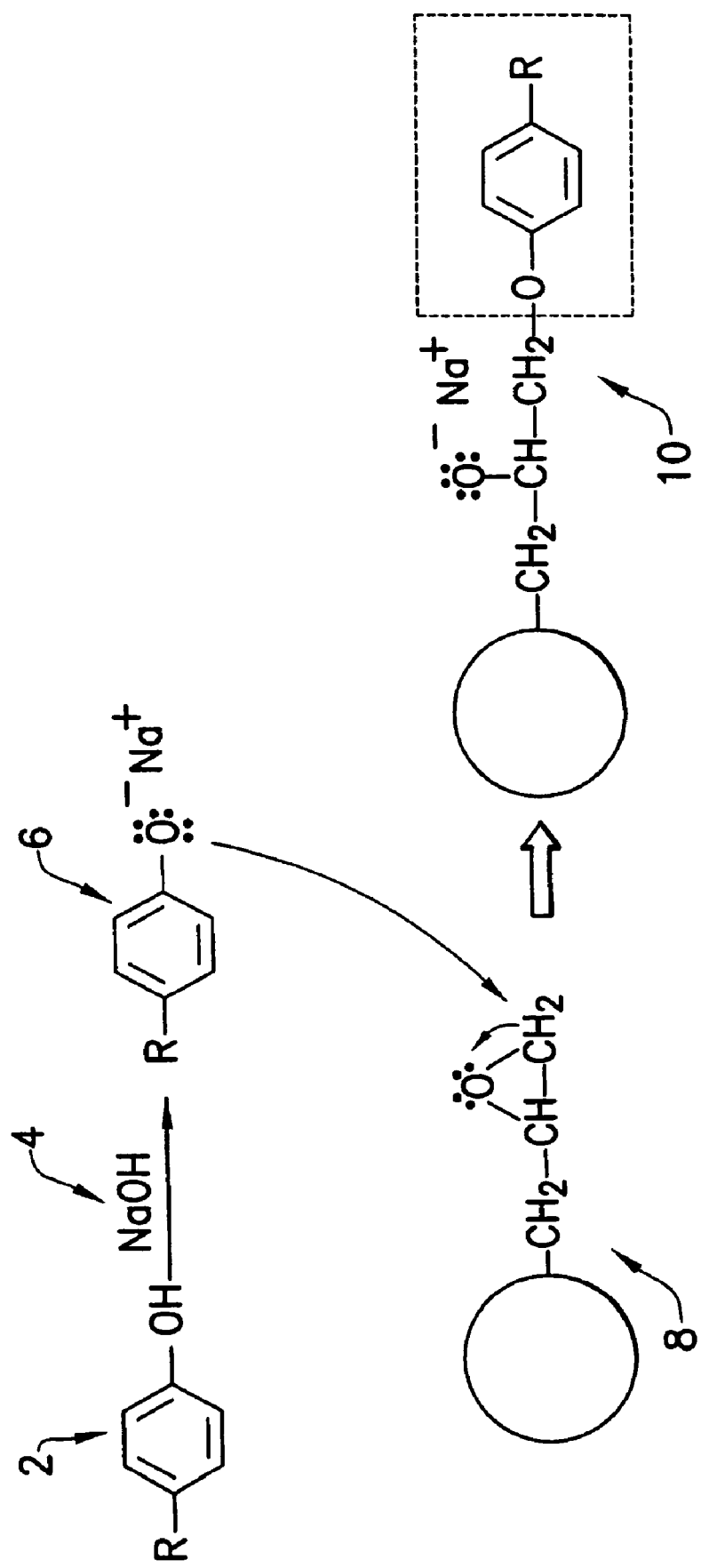
FIG. 1 depicts a method of attaching a BSP ligand to an insoluble support of sepharose beads in accordance with an aspect of the present invention.

While the present invention is satisfied by embodiments in many different forms, there will herein be described in detail embodiments of the invention, with the understanding that the present disclosure is to be considered as exemplary of the principles of the invention and is not intended to limit the invention to the embodiments illustrated and described. Numerous variations may be made by persons skilled in the art without departure from the spirit of the invention.

The present invention pertains to an apparatus for reducing the content of albumin, such as HSA, in serum, plasma and/or blood samples. In addition to HSA, reduction of albumin in samples from other mammals such as, but not limited to, bovine, canine, goat, mouse, rabbit and rats, is also contemplated. The present invention also relates to methods for reducing the content of albumin in serum, plasma and/or blood samples. The invention is also directed to albumin-depleted samples produced by the methods of the present invention. Another aspect of the present invention relates to methods for making an apparatus for reducing the content of HSA in serum, plasma and/or blood samples. The present invention further pertains to kits for reducing the content of HSA in serum, plasma and/or blood samples, which kits include an insoluble support and a ligand capable of preferentially binding albumin. Further included within the present invention are spin columns, kits including spin columns and/or components thereof, and methods for producing albumin-depleted samples using spin columns.

Apparatus for Reducing the Content of Albumin in a Sample

An apparatus in accordance with the present invention includes an insoluble support having a ligand attached thereto. The insoluble support may be contained and/or supported in or by a container such as a column, bottle, dish, filter plate, plate insert or the like. The ligand may be attached to an insoluble support either directly or indirectly (e.g., through a linker of variable length and composition).

Ligands for use in the present invention may include one or more ligands having a chemistry that permits them to bind to a particular protein, i.e., one or more ligands for which a protein has an affinity, such as a ligand capable of preferentially binding albumin. In particular, a ligand such as BSP or a salt or ester thereof may be used. BSP has the following structure:

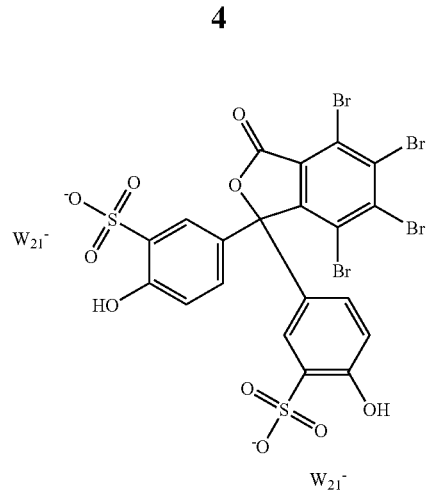

Other ligands may be used in accordance with the present invention. For example, other suitable ligands may include those for which albumin and/or other protein(s) have high binding affinity, such as Warfarin. Another suitable ligand in accordance with the present invention includes Cibacron Blue. Other examples of ligands that may tightly bind to albumin include those that are acidic and/or lipophilic. To make screening for the appropriate additional ligand more convenient, the ligand may also have an aldehyde or ketone moiety. The ligand may include compounds having at least one aromatic ring (e.g., thenyl-, benzol-, etc.), a carboxyl and/or phenolic group and a ketone or aldehyde. It should be noted that these moieties are exemplary and not exclusive, and other moieties are not meant to be excluded.

Non-limiting examples of insoluble supports in accordance with the present invention include, for example, supports for a column or a micro titre plate, standard column packing and membranes such as Sephadex membrane materials, sepharose beads, a filter plate, a matrix, affinity cartridges, and the like. For example, in the case of very small samples, an expanded surface plate may be employed as the insoluble support, where the sample is applied to the surface plate and allowed to bind, after which the supernatant (minus the bound albumin) is withdrawn by hand or with a standard robotic fluid handling station. The insoluble support is not limited to those described herein and may include any insoluble support material or matrices known to those skilled in art including, for example, those made of dextran, polythirine, or glass, in addition to standard column materials.

By way of example, an anti-albumin or anti-HSA cartridge support may be utilized using, for example, a BSP ligand attached to the cartridge support. Using a cartridge support, media may bind the albumin in a sample of human serum.

BSP may be attached to an insoluble support by any means available to those skilled in the art or those provided by certain embodiments of the present invention. According to embodiments of the present invention, methods of attaching BSP to a support may include bringing BSP or a salt or ester thereof into contact with an epoxy-activated support under alkaline conditions. Under these conditions, a hydrogen atom is removed from the BSP, thereby providing a BSP anion, which is allowed to react with the epoxy such that the BSP binds to the support. An example of such an attachment method is depicted in FIG. 1, which is also described in Example 1 below, using sepharose beads as the insoluble support, although variations using other ligands and/or supports are within the scope of the present invention.

The containers of the present invention may include any containers known to those skilled in the art, such as columns, bottles, filter plates, dishes, plate inserts and the like. Also known to those skilled in the art is the placement in and orientation of the insoluble support with respect to such containers.

Suitable containers may be modified in size and geometry for increased performance in achieving albumin depletion. The container or column geometry may have an effect on performance as set forth further below with respect to FIG. 2.

Methods for Reducing the Content of Albumin in a Sample and Methods of Producing an Albumin-Depleted Sample Methods for reducing the content of albumin, such as HSA, in samples of serum, plasma and/or blood and methods of producing an albumin-depleted sample in accordance with the present invention include providing a sample of serum, plasma and/or blood, which sample includes albumin, from which albumin is to be depleted or removed; running the sample over an insoluble support having a ligand capable of preferentially binding albumin attached thereto; and allowing albumin from the sample to bind to the ligand, thereby providing an albumin-depleted sample. The ligand may be, for example, BSP or a salt or ester thereof. The albumin-depleted sample may then be recovered. In accordance with the present invention, certain non-albumin proteins in the sample including, for example, serum proteins, may remain in the albumin-depleted sample (i.e., the serum, plasma or blood sample after it has passed over the insoluble support). The method may be optionally repeated as many times as desired using the albumin-depleted sample to obtain a sample having an even lower albumin content (i.e., a further albumin-depleted sample) than the original albumin-depleted sample. In particular, the method may include running the albumin-depleted sample over the insoluble support one or more additional times and allowing albumin from the albumin-depleted sample to bind to the ligand, thereby providing a further albumin-depleted sample.

The methods of the present invention may also include a means for handling a serum, plasma and/or blood sample including, for example, applying a sample to a surface plate and allowing the sample to bind to the plate.

According to an embodiment of the present invention, at least 80% by concentration (as measured by radialimmunoassay (RIA)) of the albumin from the sample binds to the ligand. According to another embodiment of the invention, at least 90% by concentration (as measured by RIA) of the albumin from the sample binds to the ligand. According to yet another embodiment of the invention, at least 95% by concentration (as measured by RIA) of the albumin from the sample binds to the ligand.

After albumin attaches to the ligand, which ligand is attached to an insoluble support, the serum proteins from the albumin-depleted sample may be collected, for example, in tubes or on plates, depending on the formatting of the apparatus and support and the sample size. For example, smaller samples may fit in a 96-well column format with collection in a 96-well receiver plate. In the case of larger samples, a more typical column may be used.

The present invention is further directed to an albumin-depleted sample obtained by methods of the present invention. For example, embodiments of the present invention include albumin-depleted samples prepared by a method, which method includes providing a sample that includes albumin, such as serum, plasma and/or blood; running the sample over an insoluble support having attached thereto a ligand capable of preferentially binding albumin, such as BSP or a salt or ester thereof; and allowing albumin from the sample to bind to the ligand, thereby providing the albumin-depleted sample.

Methods in accordance with the present invention result in increased specificity as measured by the ratio of albumin-to-protein over previous methods using different ligands and separation techniques. According to embodiments of the present invention, non-specific biding may be minimal.

Figure 2:
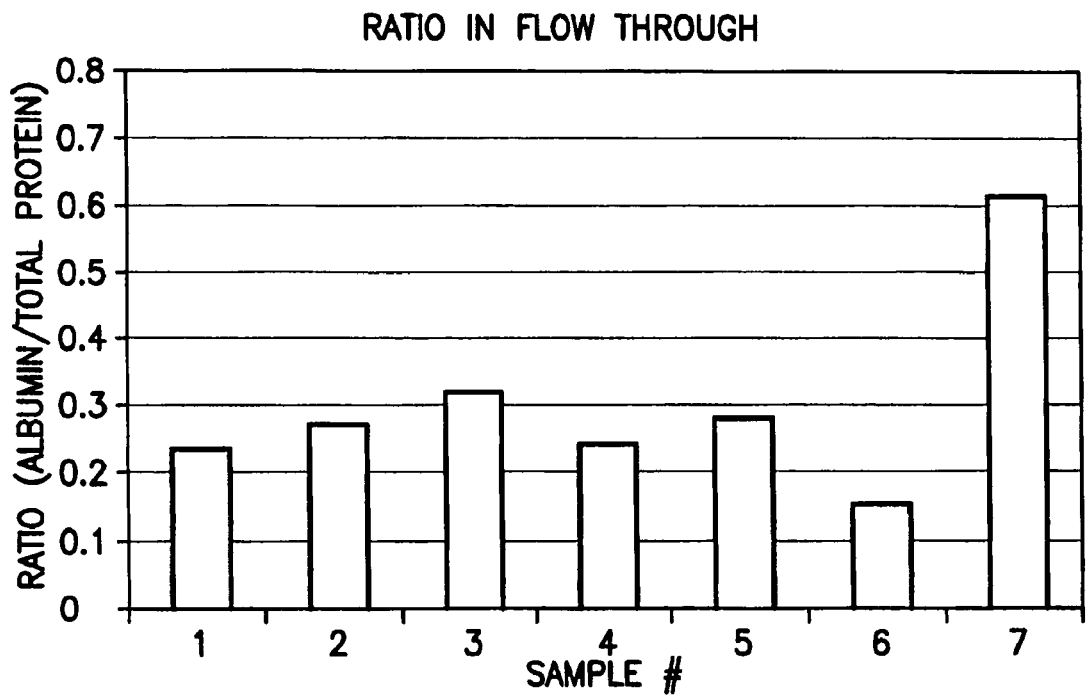
FIG. 2 is a graph depicting the relative ratios of albumin to total protein in samples that have flowed through different columns.

FIG. 2 demonstrates: (1) the importance of column geometry, which influences the amount of time the sample takes to get through the matrix; and (2) that good selectivity of albumin depletion may be obtained according to the assembly and methods of the present invention (compared on the basis of the same column). The total protein can be measured using a commercial dye binding method, and the albumin can be measured by radial immunodiffusion. The ratio of the two concentrations in the flow through of the column is presented in FIG. 2. The "flow through" represents the material that comes through the column after the sample is added and before any wash buffer is added. In experiments, 0.025 mL of human sera was mixed with 0.05 mL of PBS and applied to the column. Lanes 1 & 2 indicate that a ratio of 0.2 was obtained with the BSP matrix (i.e., BSP attached to an insoluble support) in the Biorad column, which was better than the ratio of about 0.3 for the Blue Sephadex beads in a Biorad column (lane 3) and equivalent to the Montage resin in a Biorad column (lane 5). Comparing lane 1 to lane 2 indicates that more BSP matrix in the column improves the albumin-to-protein ratio. Comparing lanes 4 and 6 to 3 and 5, respectively, indicates that for two distinct resins, the albumin-to-protein ratio is improved with the Montage column, which has a slower flow rate and, hence, a longer contact time for the sample on the column.

Figure 3:
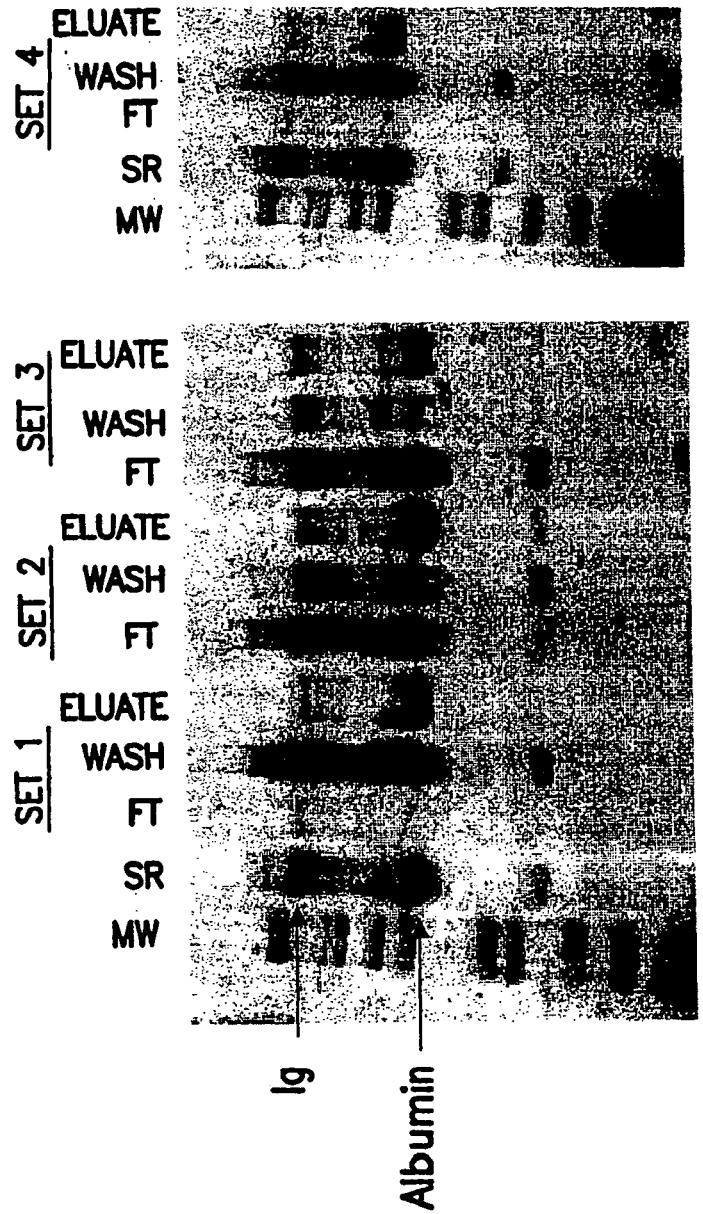
FIG. 3 depicts gels from several columns using the assembly and methods of the present invention. The gels show the presence of proteins in serum, flow through, eluate and wash.

FIG. 3 depicts SDS gels of the material from several columns. The "MW" lanes are molecular weight markers. The "SR" lanes are lanes with the serum to demonstrate what was put on the columns. The "FT" are the flow through lanes. The wash lanes are the second application to the column with the same buffer as sample. The "EL" (eluate) lanes are the third application to the column using a higher salt concentration to eluate the albumin from the column. The flow through is what the user will be using, i.e., the albumin-depleted serum. Sets 1 and 4 indicate reduced albumin in the wash and fewer "other" proteins in the elute with the albumin. Sets 2 and 3 show that the Montage resin performance is influenced by the type of column in which it is packed and that there are a number of bands of other proteins in the eluate fraction. These are proteins that may be of interest to the user.

Figure 4:
FIG. 4 depicts proteins in serum, flow through, eluate and wash using the assembly and methods of the present invention (BD).
Figure 5:
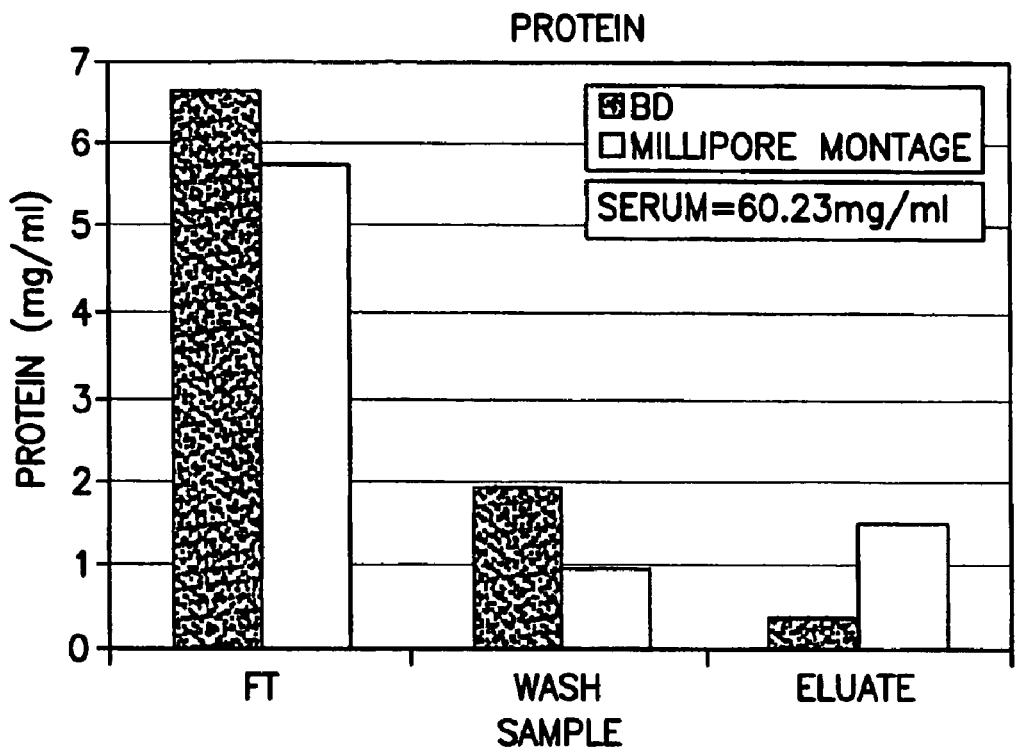
FIG. 5 depicts the actual concentration of protein in flow through, wash and eluate samples according to the methods of the present invention (BD).
Figure 6:
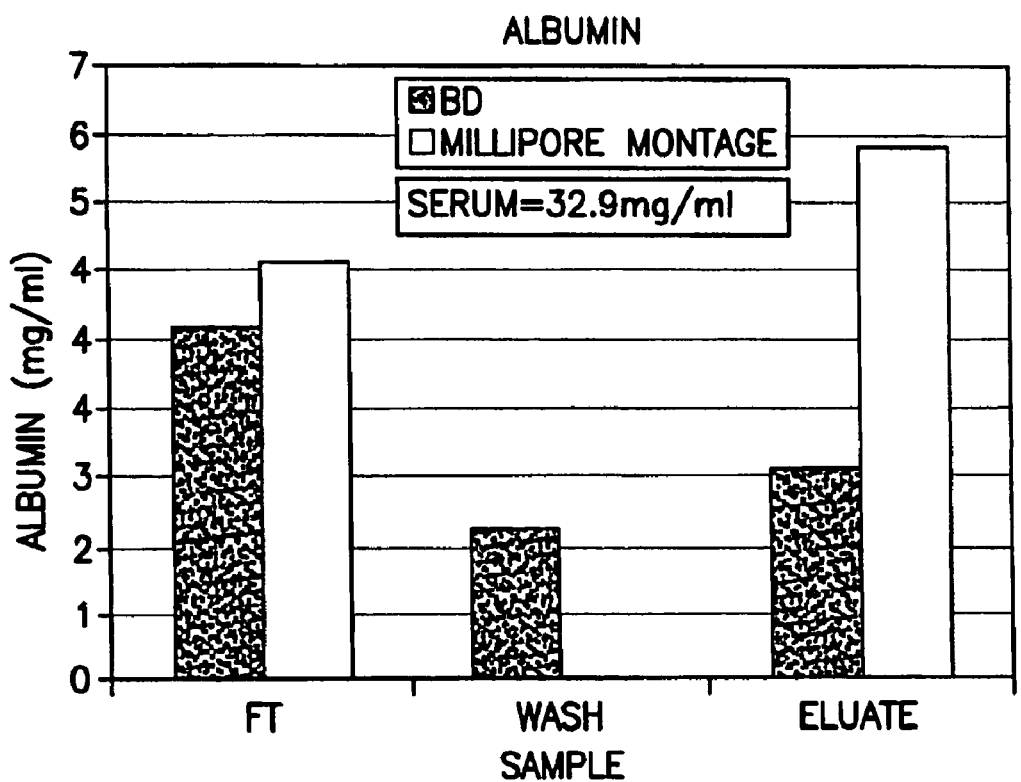
FIG. 6 depicts the actual concentration of albumin in flow through, wash and eluate samples according to the methods of the present invention (BD).

FIGS. 4-6 depict similar data to those shown in FIGS. 2 and 3, but from a different experiment with a new batch of BSP matrix to demonstrate both reproducibility of the resin synthesis and the albumin depletion. In FIGS. 5 and 6, the actual concentrations of protein and albumin are shown, respectively, rather than the ratios depicted in FIG. 2. The sample according to the present invention (the BD sample) has a 95% reduction in the concentration of the albumin in the flow through and the ratio of albumin to protein in the flow through is about 0.15. The Montage sample has slightly less protein and slightly more albumin for a ratio of about 0.21. The Montage eluate indicates more "other" proteins being bound to the resin than with the BSP resin suggesting better selectivity for the BSP resin.

Methods for Making an Apparatus for Reducing the Content of Albumin in a Sample

Another aspect of the present invention includes methods for making an apparatus for reducing the content of albumin, such a HSA, in serum, plasma and/or blood samples. The methods include attaching a ligand to an insoluble support. Generally, embodiments of the present invention include methods of binding a ligand capable of preferentially binding albumin, such as BSP or salts or esters thereof, to an insoluble support, which methods include bringing the ligand into contact with an epoxy-activated insoluble support under alkaline conditions to produce a ligand anion, and allowing the ligand anion to react with the epoxy, such that the ligand binds to the insoluble support. The support may be, for example, a macroparticle matrix capable of separating proteins from a sample run over the matrix. By way of non-limiting example, the support may be sepharose beads, and the ligand may be BSP or a salt or ester thereof, in which case the method may include the method described in Example 1 below.

Removal of Other Proteins in Conjunction with Albumin Removal

Apparatuses in accordance with the present invention may be used in combination with a cartridge or other apparatus capable of removing other proteins from samples of serum, plasma and/or blood. According to certain embodiments of the invention, an apparatus in accordance with the present invention, which includes an insoluble support having a ligand attached thereto for binding albumin, is used in conjunction with an apparatus having a support adapted to remove one or more other proteins from a sample. Non-limiting examples of proteins that may be removed in accordance with the present invention include albumin, IgG, IgA, alpha and beta lipoproteins, alpha1-antitrypsin, alpha2-macroglobulin, fibrinogen, transferrin, haptoglobin, complement C3, and the like. Accordingly, the present invention includes apparatuses that are adapted to remove one or more of these or other proteins from a sample. According to certain embodiments, albumin and one or more other proteins can be removed in one step or they can be removed in multiple steps in any order. A non-limiting example according to these embodiments includes using affinity chromatography cartridges as supports for binding HSA and/or IgG. Cartridges according to certain embodiments of the invention may be specific and exhibit little to zero non-specific binding, and may also have other desirable characteristics such as high throughput processing, cleanability, and reusability.

The present invention also includes methods for producing a protein-depleted sample such as, for example, a sample depleted of albumin and one or more additional proteins, such as IgG. Methods according to these embodiments may include, for example, providing a sample, which sample includes albumin and one or more additional proteins; running the sample over an insoluble support having a ligand capable of preferentially binding albumin; allowing albumin from the sample to bind to the ligand; running the sample over one or more insoluble supports adapted to be capable of preferentially binding to a ligand or otherwise removing one or more non-albumin proteins from the sample; and allowing the one or more non-albumin proteins to be removed from the sample, thereby providing a protein-depleted sample. The methods of the present invention may include running the protein-depleted sample over one or more of the insoluble supports one or more additional times and allowing additional proteins from the protein-depleted sample to be removed, thereby providing a further protein-depleted sample. The methods of the present invention may further include collecting the protein-depleted sample. Suitable supports, ligands, collection containers, and other aspects of these embodiments are as set forth throughout this application.

It should be noted that the insoluble support having a ligand capable of preferentially binding albumin and the insoluble support adapted to be capable of preferentially binding to a ligand or otherwise removing one or more non-albumin proteins from the sample, may be the same or separate supports and the running of the sample over this support(s) may be performed in one or multiple steps. Moreover, the order of running the sample over different supports and separating out different proteins is not intended to be limited by the order of the method steps recited herein. That is, the steps of running the sample over one or more other insoluble supports adapted to be capable of preferentially removing one or more non-albumin proteins from the sample and allowing the one or more non-albumin proteins to be removed from the sample may be performed before, during or after running the sample over an insoluble support having a ligand capable of preferentially binding albumin and allowing albumin from the sample to bind to the ligand.

The present invention further provides protein-depleted samples produced by the methods described herein.

Methods of the present invention may include, for example, passing a sample of serum, plasma or blood over a protein cartridge and an anti-HSA cartridge. Flow through (serum proteins) and eluted fractions (e.g., albumin and/or IgG) may then be analyzed to quantitate the removal of HSA and/or an IgG from the sample and examine the level of non-specific binding. Samples may be processed via high throughput Multi-Dimensional Liquid Chromatography systems or may be processed in a manual mode using unique cartridge format. In addition, the apparatuses according to the present invention may be used in conjunction with 2-D gels, ICAT reagent technology, LC/MS or MALDI-TOF-MS analysis.

An exemplary method of using chromatography to extract HSA in conjunction with other proteins is set forth in Example 3 below.

Albumin-Depletion Spin Columns

Figure 9:
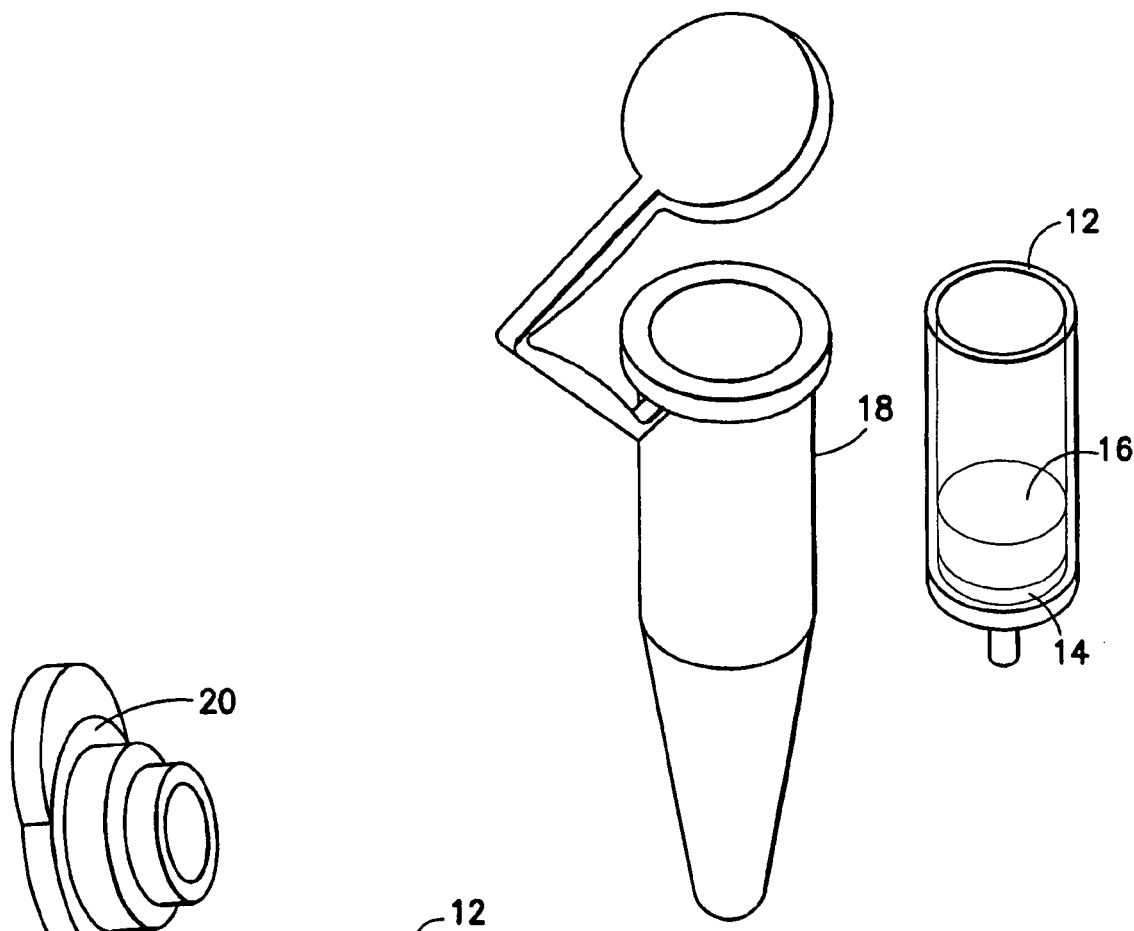
FIG. 9 depicts a spin column and inner column according to embodiments of the present invention.

Embodiments of the present invention include spin columns that may be used to reduce albumin in samples. An example of a spin column in accordance with the present invention is depicted in FIG. 9. The spin column depicted in FIG. 9 is a spin column for a standard table-top mini centrifuge; however, spin columns of other sizes and having other geometries are contemplated by the present invention. According to certain embodiments, an inner column (12) may be provided, such as that depicted in FIG. 9. According to embodiments of the invention, the inner column may optionally have a specialized column bottom (14). Albumin-binding resin (16) may be located in the inner column in contact with the specialized column bottom. The albumin-binding resin may optionally include BSP, Cibacron Blue, Warfarin or other appropriate ligand that is capable of preferentially binding albumin.

Figure 7:
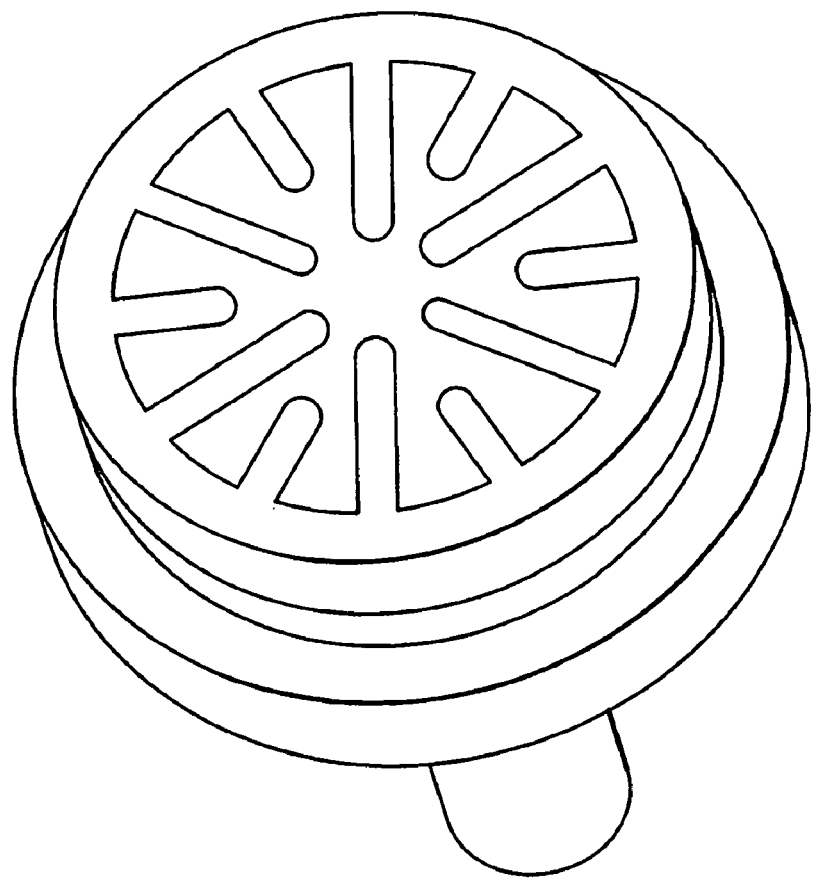
FIG. 7 depicts a top view of a column bottom according to embodiments of the present invention.
Figure 8:
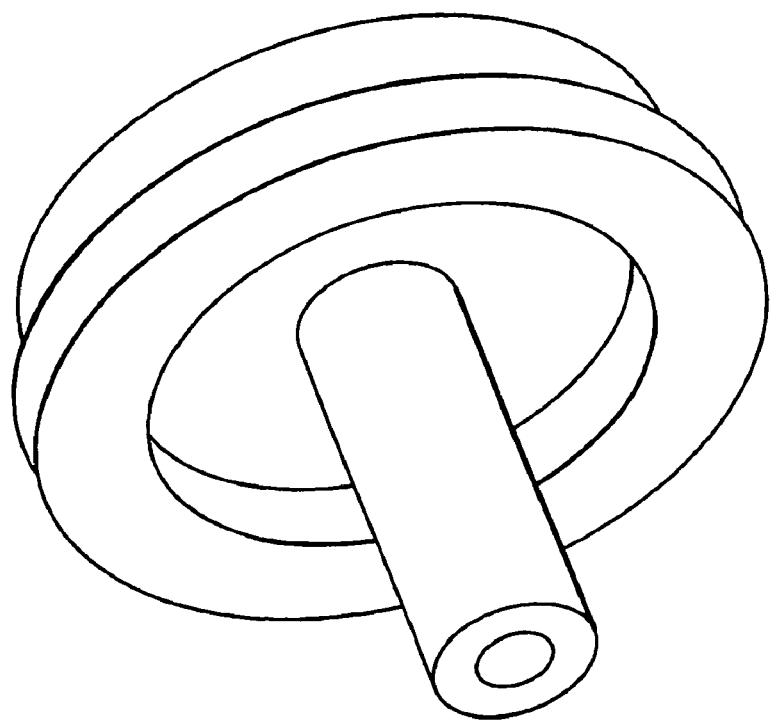
FIG. 8 depicts a bottom view of a column bottom according to embodiments of the present invention.
Figure 10:
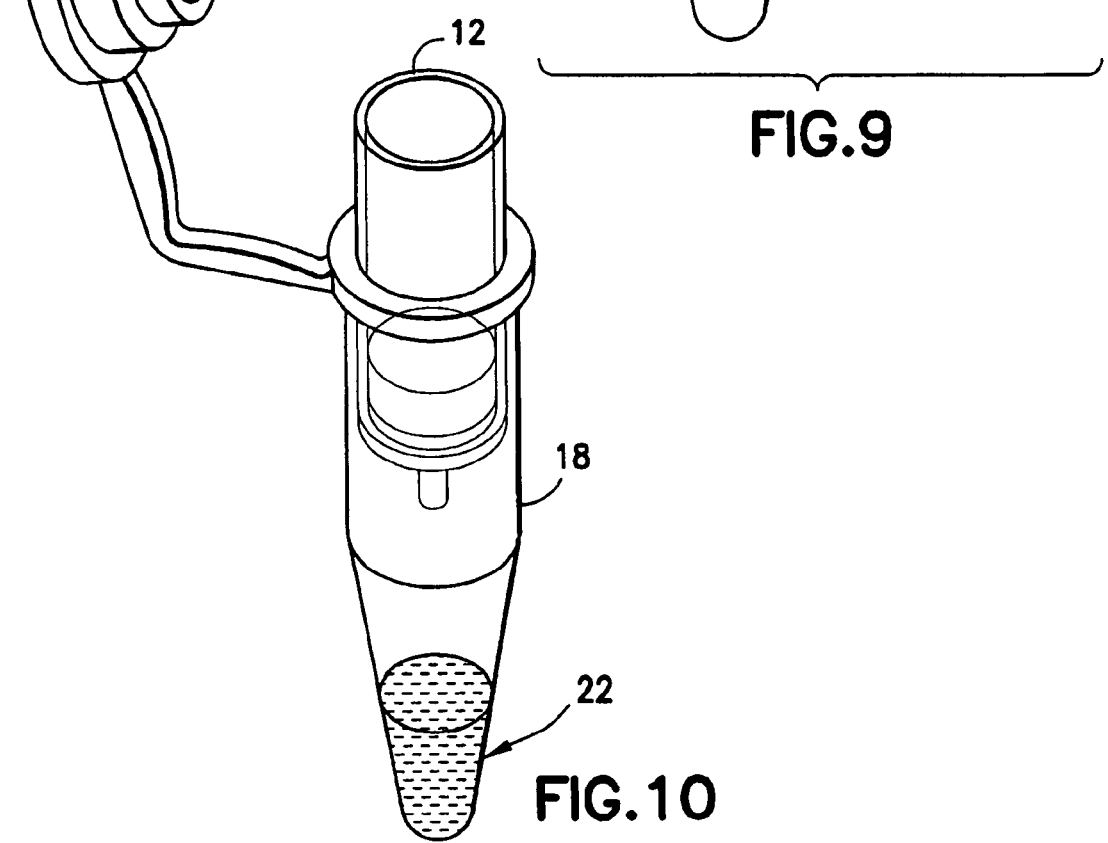
FIG. 10 depicts a spin column and inner column placed within the spin column according to embodiments of the present invention.

The specialized column bottom may have one or more flow directors and/or membrane assemblies. The column bottom may be formed into a particular geometry, for example, to prevent resin from drying up during a spin, to increase sample residence time, and/or to increase interaction of resin with the sample. A non-limiting example of a suitable specialized column bottom geometry in accordance with the present invention is depicted from different angles in FIGS. 7 and 8. As depicted in FIG. 10, the inner column (12) of the spin column is adapted to fit within a receiving tube (18). The receiving tube may have a lid (20) for example, as depicted in FIGS. 9 and 10. The lid may be configured such that it seals the receiving tube, or it may optionally be configured to seal both the inner column and the receiving tube.

Accordingly, the present invention includes a spin column comprising a receiving tube and an inner column adapted to fit within the receiving tube. The inner column includes an albumin-binding resin and, optionally, a column bottom, where the column bottom is in contact with the albumin-binding resin. The receiving tube optionally has a lid. According to further embodiments, the spin column includes a lid adapted to seal the receiving tube and, optionally, further adapted to seal the inner column. The inner column may have a rim to prevent it from entering further than desired into the receiving tube. According to certain embodiments, the albumin-binding resin comprises one or more ligands capable of preferentially binding albumin, where such ligands may be one or more ligands selected from the group consisting of BSP, Cibacron Blue, Warfarin, and salts or esters thereof. Spin columns in accordance with the present invention may optionally include one or more other protein-binding ligands to remove albumin and/or one or more other proteins from the sample.

According to methods of the present invention, a sample containing albumin is obtained and placed into the spin column, the sample is maintained in the spin column, and optionally the spin column is spun in a centrifuge. An albumin-depleted protein sample, which emerges from the specialized column bottom, may be collected in the bottom of the spin column (22). According to certain embodiments, methods for producing an albumin-depleted sample may include providing a spin column, which spin column comprises a receiving tube and an inner column adapted to fit within said receiving tube, wherein the inner column comprises a column bottom and an albumin-binding resin, and wherein the column bottom is in contact with the albumin-binding resin; placing a sample that includes albumin in the inner column of the spin column; and maintaining the sample in the spin column for a period of time sufficient for albumin from the sample to bind to the albumin-binding resin in the inner column and to allow the sample minus the bound albumin to flow through the inner column, thereby producing an albumin-depleted sample (flow through). The column may optionally be spun in a centrifuge. The column may optionally be washed before collecting the albumin-depleted sample. If desired, the bound fraction (albumin and other retained proteins) can be recovered using a stripping solution. A lid may be attached to the receiving tube or may be independent of the receiving tube. For example, a lid may be attached to a ring that is slid up the outside of the receiving tube.

The methods of the present invention may further include collecting the albumin-depleted sample. The albumin-depleted sample may optionally be reinserted into the inner column one or more times and sample maintained in the spin column for a period of time sufficient for additional albumin from the sample to bind to the albumin-binding resin in the inner column, before being optionally recovered and transferred to a separate clean tube or other collection device. If the inner column is in a kit separate from the receiving tube, the methods may include inserting the inner column into the receiving tube.

The albumin-binding resin may include one or more ligands capable of preferentially binding albumin, such as BSP, Cibacron Blue, Warfarin, and salts or esters thereof. Examples of samples in accordance with these embodiments may include plasma, serum and blood.

The eluate and/or bound fraction may be analyzed upon removal from the spin column by methods known to those in the art to determine various things, such as percent albumin depletion and the amount of non-specific binding. Such methods may include those known to persons skilled in the art including, for example, liquid chromatography, SDS-PAGE and RIA methods depending on whether it is the eluate or the bound fraction being analyzed and for what purpose it is being analyzed.

Kits

The present invention further pertains to kits that may be used for reducing the content of albumin in a sample, which kits include an insoluble support and a ligand capable of preferentially binding albumin. The ligand may optionally be attached to the insoluble support in the kits of the present invention. According to certain embodiments of the invention, the ligand in the kits may include BSP or a salt or ester thereof.

Kits according the present invention may optionally include a container as described herein, a support as described herein, and/or a collection apparatus as described herein such as, for example, collection tubes, which collection apparatus may be used for collecting albumin-depleted sample.

The present invention may also include one or more additional insoluble supports adapted to be capable of binding one or more non-albumin proteins. A non-limiting example of one or more additional insoluble supports may include a support adapted to bind IgG, such as a Protein A cartridge, a Protein G cartridge, and/or a combination Protein A and Protein G cartridge.

Kits in accordance with the present invention may optionally include affinity columns, microcentrifuge tubes, buffers (such as equilibration, wash and/or stripping buffers), and/or reagents in various sizes and amounts, for example, for running different types and amount of samples.

The present invention may further include kits that include albumin-depletion spin columns or components thereof. In particular, kits in accordance with the present invention may include a receiving tube and an inner column, wherein the inner column comprises an albumin-binding resin, and optionally, a column bottom, and wherein the spin column optionally includes a lid. According to certain embodiments, the albumin-binding resins may include one or more ligands capable of preferentially binding albumin such as, for example, BSP, Cibacron Blue, Warfarin, or salts or esters thereof. Kits in accordance with the present invention may also include a stripping solution for recovering the bound fraction.

The following examples illustrate specific embodiments of the invention. The examples set forth herein are meant to be illustrative and should not in any way serve to limit the scope of the claimed invention. As would be apparent to skilled artisans, various changes and modifications are possible and are contemplated within the scope of the invention described.

EXAMPLES

Example 1

Preparation of Sulfobromophthalein Conjugated Sepharose Gel for Albumin Depletion A method of attaching BSP to an insoluble support of sepharose beads in accordance with the present invention is depicted in FIG. 1. As shown in FIG. 1, BSP (2) is brought into contact with epoxy-activated sepharose beads (8) under acidic conditions (e.g., using sodium hydroxide (4)). Under these conditions, a hydrogen atom from the BSP (2) is removed, and the BSP having an anion (6) is able to react with the epoxy to form a BSP ligand attached to a sepharose bead insoluble support (10). The beads having a BSP ligand attached thereto are then supported within a column to form an assembly in accordance with an aspect of the invention.

In particular, the method may proceed as follows:

Epoxy-activated Sepharose 6B is obtained from a commercial source.

Sulfobromophthalein sodium salt is obtained from a commercial source

Coupling of Sulfobromophthalein to 1 g of Epoxy-activated Sepharose 6B is performed using the following steps:

Weigh out 1 g of Epoxy-activated Sepharose 6B and suspend it in pure water. The gel swells immediately. Wash the gel twice with pure water.

Dissolve 0.5 g of Sulfobromophthalein in 5 mL 0.1 M NaOH.

Coupling: Mix the Sulfobromophthalein solution with the gel. Incubate for 48 hours on a shaker at room temperature.

Wash away excess Sulfobromophthalein using pure water.

Block any remaining active groups: Transfer the gel to 1 M ethanolamine pH 8.0.

Incubate overnight on a shaker at room temperature.

Wash the product thoroughly with pure water.

Example 2

Method for Reducing the Content of Albumin in a Sample

A sample of human serum is obtained. The sample is diluted for example with PBS. The sample is then run over sepharose beads having a bromosulfophthalein ligand attached thereto, which beads are contained within an affinity column. As noted previously, the column geometry or design may have an effect on the efficacy of albumin-depletion; therefore, the geometry and design of the column is selected so as to optimize the effectiveness of the BSP matrix. Albumin from the sample attaches to the BSP ligand. What is left of the sample after it has run through the column is substantially albumin-depleted. The albumin-depleted sample is then collected.

Example 3

Chromatography

A method in accordance with the present invention of selectively removing HSA and one or more other proteins from blood, serum or plasma is provided using chromatography, such as using the VISION Workstation.

According to one example, 70 µL samples of human serum diluted 1:10 with PBS is passed through a 0.2 mL Protein A and/or Protein G cartridge and then the flow through fraction is diluted to 400 µL. Then 100 µL of the diluted Protein A and/or Protein G flow through fraction is applied to a 0.2 mL Anti-HSA cartridge (having a BSP ligand attached thereto) at a flow rate of 0.5 mL/minute.

According to certain embodiments, a sample of blood, serum or plasma is run over a Protein G cartridge to remove IgG from the sample, and then the sample is run over a cartridge having BSP attached thereto operated on the VISION™ Workstation. The separations can be performed separately or in tandem in minutes using an automated workstation, such as the VISION™ Workstation, as well as being performed manually using a syringe inlet adapter.

Protein concentrations from eluted fractions may be determined using, for example, a Bradford assay. Protein may be analyzed by SDS-PAGE, and the proteins may be visualized by colloidial Coomassie stain. Other forms of analysis may also be used, such as 2-D gel analysis, peptide mass fingerprinting, and other methods known to those skilled in the art to determine protein concentrations before and after the methods of the present invention and to determine protein concentration in the initial sample, in the eluted fractions, and in the flow through. Removal of albumin and IgG can be quantified, for example, using commercially available ELISA assays.

Example 4

Albumin-Depletion Spin Columns

An apparatus in accordance with the present invention is provided in the form of a spin column as depicted in FIG. 9. The spin column depicted in FIG. 9 is a spin column for a standard table top mini centrifuge; however, spin columns of other sizes and geometries are contemplated by the present invention. In the apparatus depicted in FIG. 9, an inner column (12) is provided having a specialized column bottom (14). Albumin-binding resin including BSP (16) is located in the column in contact with the specialized column bottom having the geometry depicted in FIGS. 7 and 8. The specialized column bottom has one or more flow directors and/or a membrane assembly and is formed into a particular geometry to prevent resin from drying up during a spin, to increase sample residence time, and/or to increase interaction of resin with the sample. The inner column is adapted to fit within a receiving tube (18). The receiving tube may have a lid (20) for example, as depicted in FIGS. 9 and 10.

A sample of serum-containing albumin is obtained, diluted with equilibration buffer and placed into the receiving tube of the spin column. The inner column is then placed within the receiving tube and the lid of the receiving tube is closed. The sample is maintained in the spin column for a time sufficient for albumin in the sample to bind to the BSP in the inner column. The spin column may optionally be spun in a centrifuge (for example, for two minutes at 2000 rpm), thereby producing an albumin-depleted sample that is collected in the receiving tube, which may then be removed from the receiving tube. The albumin-depleted sample may then be reinserted into the column and maintained in the spin column and/or re-centrifuged one or more times before being recovered and transferred to a separate clean tube. According to another embodiment, the sample is diluted and placed into the inner column of a spin column, the lid of the receiving tube is closed and the spin column is centrifuged for a time sufficient for albumin in the sample to bind to BSP in the inner column.

Example 5

Procedure for Albumin Depletion Using a Column

Albumin is depleted from a sample of serum or plasma in accordance with embodiments of the present invention as follows:

Sample Dilution

Step 1: Dilute serum or plasma sample in PBS with a recommended ratio of one part serum or plasma to two parts PBS.

For example: Add 25 μL of serum or plasma to 50 μL of PBS.

Column Equilibration

Step 2: Add 400 μL of PBS to the column. Place the column in a collection tube and centrifuge for two minutes at 2000 rpm (approximately 500×g at a 7 cm average rotor radius).

Step 3: Discard the buffer from the collection tube.

Step 4: Repeat steps 2-3.

Albumin Depletion

Step 5: Add 75 μL of diluted serum or plasma sample to the equilibrated column. Place the column in a new collection tube and wait five minutes. Centrifuge for two minutes at 2000 rpm.

Step 6: Recover the flow through from the collection tube and add it back into the column. Wait five minutes. Centrifuge for two minutes at 2000 rpm. The flow through can now be analyzed.

Note: The sample is processed through the Albumin-Deplete Column of the present invention at least two times.

Column Wash

Step 7: Add 200 μL of PBS to the column. Place the column in a new collection tube and centrifuge for two minutes at 2000 rpm.

Step 8: Add another 200 μL of PBS to the column. Place the column in the same collection tube and centrifuge for two minutes at 2000 rpm. The wash can now be analyzed.

Note: Different concentrations and volumes may be used in accordance with the present invention.

The following human serum samples were treated with the BD™ Albumin-Deplete Columns according to the present invention:

Diluted human serum sample A: 50 μL human serum+25 μL PBS

Diluted human serum sample B: 35 μL human serum+40 μL PBS

Diluted human serum sample C: 25 μL human serum+50 μL PBS

Figure 11:
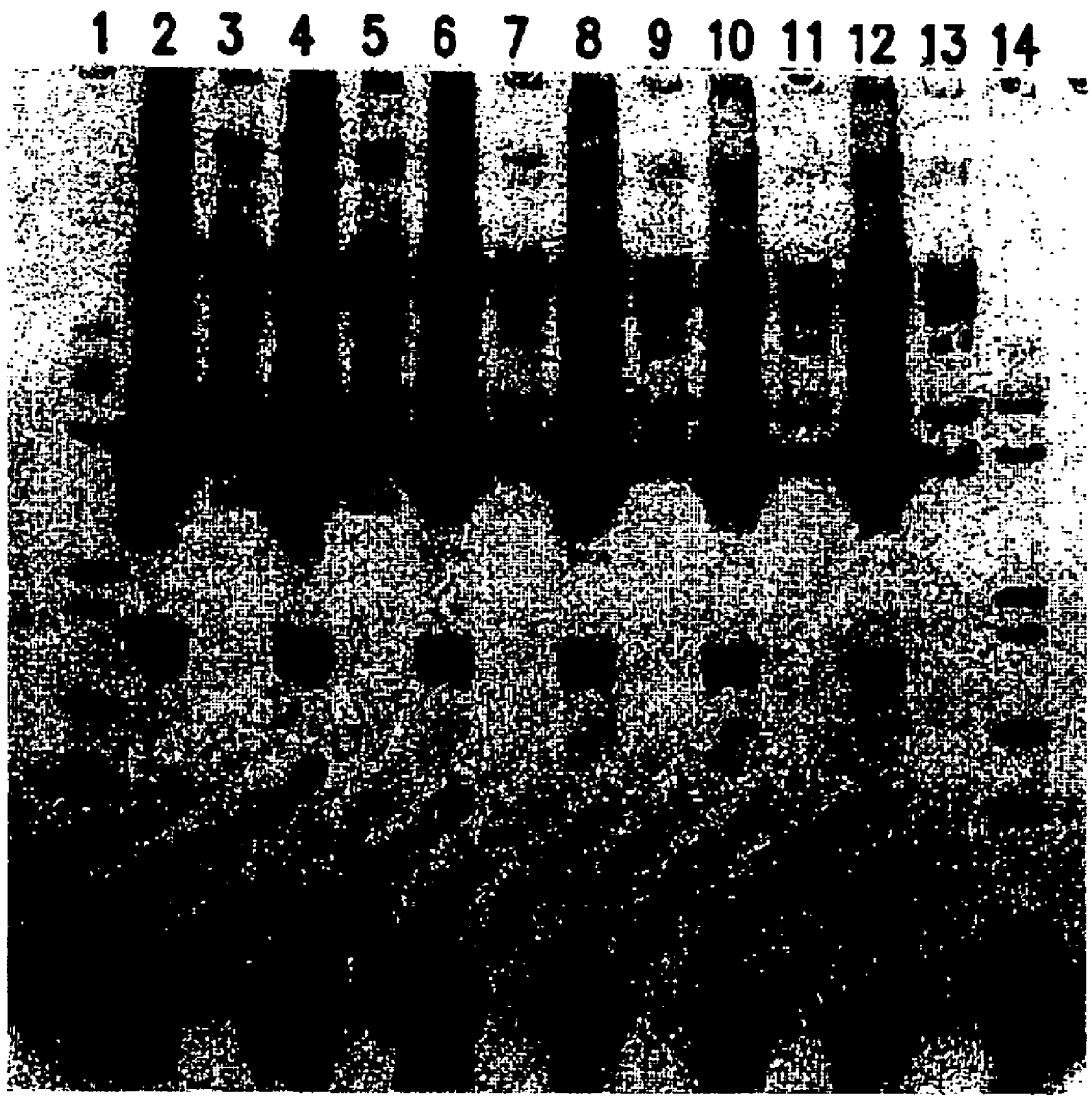
FIG. 11 depicts a gel showing the reproducibility and efficiency of albumin removal of three samples, each having a different concentration of human serum to phosphate-buffered saline (PBS).

FIG. 11 depicts a 1-D gel showing the reproducibility and efficiency of albumin removal. The numbered columns 1-14 in FIG. 11 correspond to the following:

1—Standard
2—Diluted human serum sample A
3—Flow Through of sample A, replicate 1
4—Diluted human serum sample A
5—Flow Through of sample A, replicate 2
6—Diluted human serum sample B
7—Flow Through of sample B, replicate 1
8—Diluted human serum sample B
9—Flow Through of sample B, replicate 2
10—Diluted human serum sample C
11—Flow Through of sample C, replicate 1
12—Diluted human serum sample C
13—Flow Through of sample C, replicate 2
14—Standard FIG. 11 demonstrates that when a diluted human serum sample in a concentration of 1:2 (serum:PBS) is used (see, e.g., cols. 10 and 12) the protein flow through (see, e.g. cols. 11 and 13) is less than when the sample has a higher serum to albumin ratio.

Figure 12:
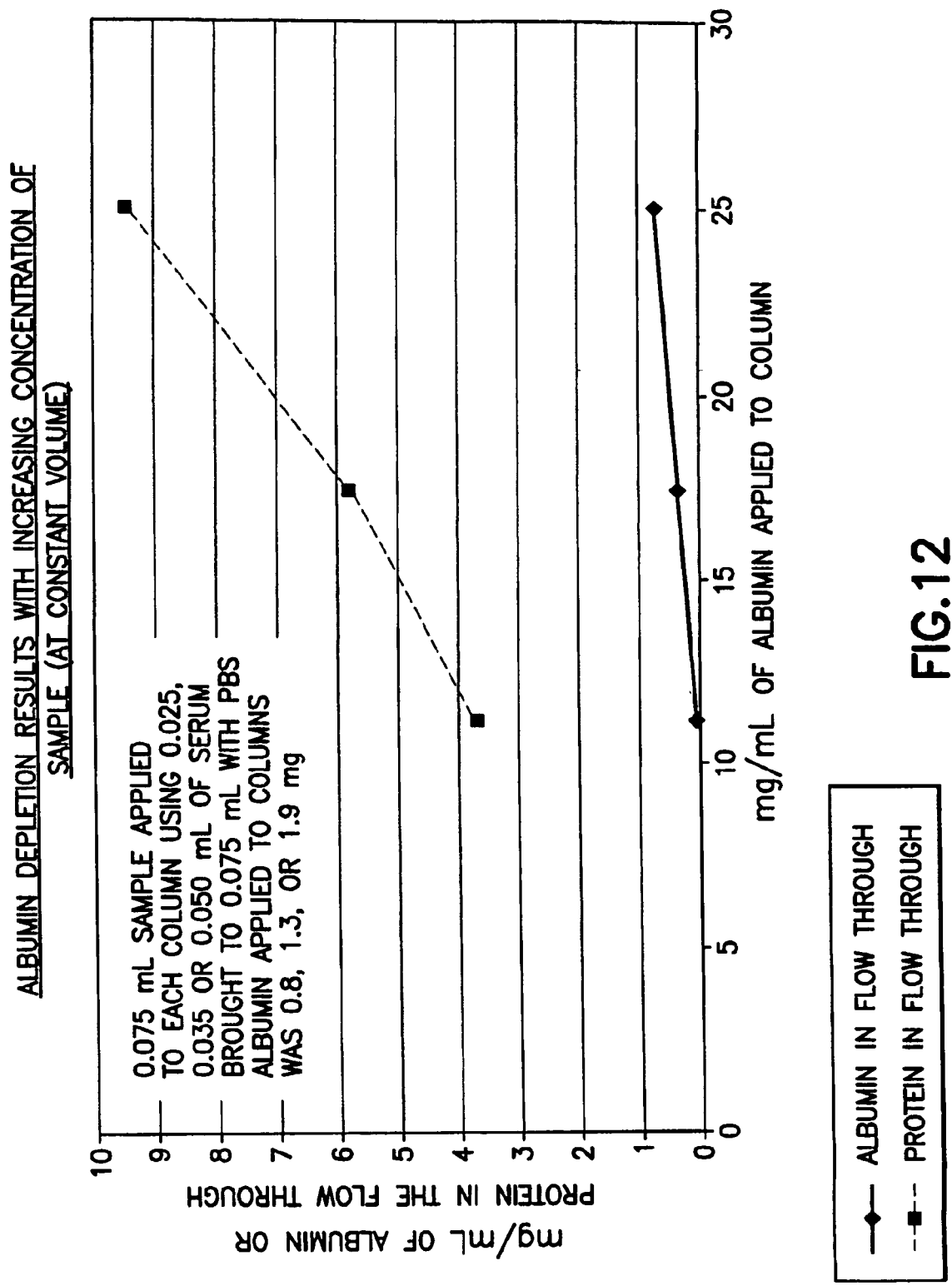
FIG. 12 depicts a graph showing how total protein and albumin depletion resulting from passing a sample through a column of the present invention changes as a function of concentration of serum to PBS.
Figure 13:
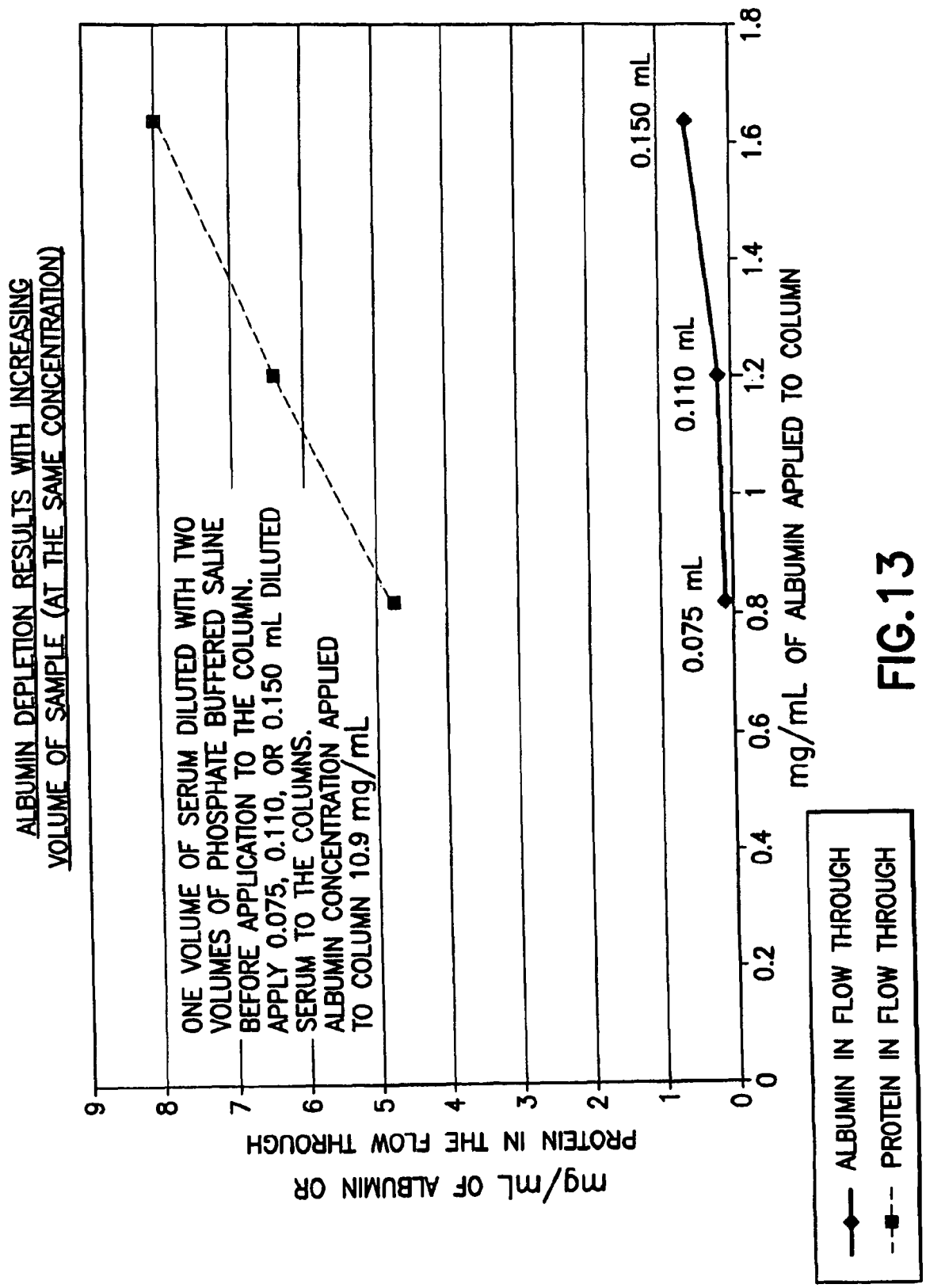
FIG. 13 depicts how increasing the volume of a sample increases the amount of albumin and total protein that flow through a column according to the present invention.

FIG. 12 is a graph depicting the results of albumin and protein in the flow through after a sample of human serum in combination with PBS is passed through an albumin-deplete column according to the present invention. Each graphed sample has a total volume of 0.075 mL (75 μL), but the concentration of sample increases from left to right on the graph. For example, the two left-most points on the graph depict the concentrations of protein and albumin after a sample of 25 μL human serum and 50 μL PBS is passed through the albumin-deplete column. The next two points depict the concentrations of protein and albumin after a sample of 35 μL human serum and 40 μL PBS is passed through the column. The right-most points relate to samples of 50 μL human serum and 25 μL PBS. FIG. 12 shows that when a sample having an approximately 1:2 ratio of human serum to PBS is applied to an albumin-deplete column, the amount of albumin and total protein flowing through the column is reduced as compared to when samples having higher ratios of human serum to PBS are applied to the column. This demonstrates the versatility of the system, depending on the users experimental goals. The left side of FIG. 12 demonstrates conditions to obtain a lesser amount of albumin in the system while increasing the sample concentration and moving to the right demonstrates conditions that can achieve a greater increase in protein concentration FIG. 13 is a graph depicting how increasing the volume of sample increases the amount of albumin and total protein that flow through a column according to the present invention, when the concentration of human serum to PBS is held constant at 1:2. As depicted in FIG. 13, as the sample volume increases from 0.075 mL to 0.110 mL to 0.150 mL, the amount of both albumin and total protein flowing through the column rise. This demonstrates the versatility of the system, depending on the users experimental goals. The left side of FIG. 12 demonstrates conditions to obtain a lesser amount of albumin in the system while increasing the sample volume and moving to the right demonstrates conditions that can achieve a greater increase in protein concentration than albumin concentration.

I claim:

1. A method for producing an albumin-depleted sample, comprising: providing a sample, which sample includes albumin and phosphate-buffered saline;

running the sample over an insoluble support having attached thereto a ligand comprising at least one hydroxyl group, said ligand consisting of bromosulfophthalein or a salt or ester thereof, said ligand attached to said insoluble support via an epoxy linkage; and allowing albumin from the sample to bind to the ligand, thereby providing the albumin-depleted sample.

2. The method of claim 1, further comprising collecting the albumin-depleted sample.

3. The method of claim 1, further comprising:

running the albumin-depleted sample over the insoluble support one or more additional times; and allowing albumin from the albumin-depleted sample to bind to the ligand, thereby providing a further albumin-depleted sample.

4. The method of claim 3, further comprising collecting the further albumin-depleted sample.

5. The method of claim 1, wherein the sample is selected from the group consisting of serum, plasma, and blood.

6. The method of claim 1, wherein the albumin is human serum albumin.

7. A method for producing a protein-depleted sample, comprising:

providing a sample, which sample includes albumin and one or more additional proteins and phosphate-buffered saline; running the sample over an insoluble support having a ligand comprising at least one hydroxyl group, said ligand consisting of bromosulfophthalein or a salt or ester thereof, said ligand attached to said insoluble support via an epoxy linkage, allowing albumin from the sample to bind to the ligand;

running the sample over one or more insoluble supports adapted to be capable of preferentially removing one or more non-albumin proteins from the sample; and allowing the one or more non-albumin proteins to be removed from the sample, thereby providing a protein-depleted sample.

8. The method of claim 7, further comprising collecting the protein-depleted sample.

9. The method of claim 7, further comprising:

running the protein-depleted sample over one or more of the insoluble supports one or more additional times; and allowing additional proteins from the protein-depleted sample to be removed, thereby providing a further protein-depleted sample.

10. The method of claim 7, wherein the steps of running the sample over one or more other insoluble supports adapted to be capable of preferentially removing one or more non-albumin proteins from the sample and allowing the one or more non-albumin proteins to be removed from the sample are performed before running the sample over an insoluble support having a ligand capable of preferentially binding albumin and allowing albumin from the sample to bind to the ligand.

11. The method of claim 7, wherein the albumin is human serum albumin.

12. The method of claim 5, wherein said serum is present in a concentration of a 1:2 ratio of serum to phosphate-buffered saline.

13. The method of claim 7, wherein the sample is selected from the group consisting of serum, plasma, and blood.

14. The method of claim 13, wherein said serum is present in a concentration of a 1:2 ratio of serum to phosphate-buffered saline.

* * * * *